United States Patent
Towliat

(12) 
(10) Patent No.: US 6,200,285 B1
(45) Date of Patent: Mar. 13, 2001

(54) AIRWAY OPENER

(76) Inventor: Faye F. Towliat, 2455 Camino de Sol, Fullerton, CA (US) 92833

( * ) Notice: Subject to any disclaimer, the term of this patent is extended or adjusted under 35 U.S.C. 154(b) by 0 days.

(21) Appl. No.: 09/275,630

(22) Filed: Mar. 24, 1999

(51) Int. Cl.⁷ .................................................. A61F 5/00
(52) U.S. Cl. ........................................ 602/18; 128/DIG. 23
(58) Field of Search ............................ 128/845, 846, 128/869, 870, DIG. 23; 602/5, 17, 18

(56) References Cited

U.S. PATENT DOCUMENTS 3,276,444 * 10/1966 Rice ........................................ 128/75
5,494,048 * 2/1996 Carden ..................................... 602/32
5,785,670 * 7/1998 Hiebert ..................................... 602/18

* cited by examiner

*Primary Examiner*—Michael A. Brown
(74) *Attorney, Agent, or Firm*—Price and Gess

(57) ABSTRACT

A cervical collar for holding open the airway of a post-anesthesia patient having first and second flexible foam arm portions wrappable about the patient's neck and a central foam portion shaped to be positioned on the patient's neck in a manner to apply pressure to the patient's chin so as to maintain his or her airway open.

12 Claims, 2 Drawing Sheets

AIRWAY OPENER

BACKGROUND OF THE INVENTION

1. Field of the Invention

The subject invention relates to medical apparatus and, more particularly, to an airway opener particularly useful in post-anesthesia applications.

2. Description of Related Art

During post-operative procedures, it is necessary to hold open the airway of an anesthetized unconscious patient. For many years and, in fact today, this is done by a nurse, or other attendant, who must hold the patient's chin in an appropriate position.

A proposed device for holding a patient's airway open during surgical procedures has been disclosed in Carden, U.S. Pat. No. 5,632,283. The device of this patent employs a tether which extends around the patient's chin and ties to a pylon. Various other neck support devices are known in the prior art, however, as with the Carden device they are not suitable for post-operative use. Moreover, such prior art neck support apparatus typically includes a relatively large number of parts, is expensive and complicated to use, and does not properly accommodate the needs of the post-operative patient.

SUMMARY OF THE INVENTION

According to the invention, a cervical collar is provided which is removably attachable about the neck of the patient and shaped to lift the angle of the lower jaw to an appropriate position where the patient's airway is open.

BRIEF DESCRIPTION OF THE DRAWINGS

The just summarized invention, as well as its objects and advantages, will now be described in the following specification as illustrated in the accompanying drawings, wherein.

DETAILED DESCRIPTION OF THE PREFERRED EMBODIMENTS

The following description is provided to enable any person skilled in the art to make and use the invention and sets forth the best modes contemplated by the inventor of carrying out her invention. Various modifications, however, will remain readily apparent to those skilled in the art, since the general principles of the present invention have been defined herein specifically to provide a readily manufacturable and easily used cervical collar apparatus.

Figure 1:
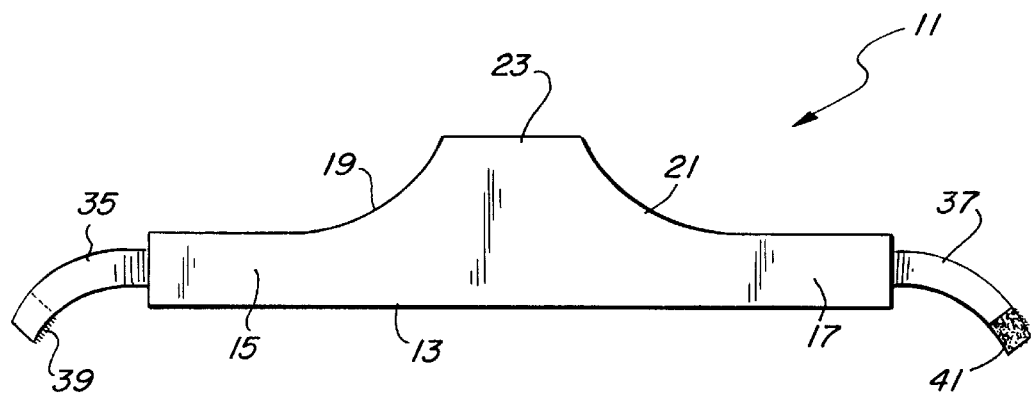
FIG. 1 is a front view of a cervical collar according to a preferred embodiment.
Figure 2:
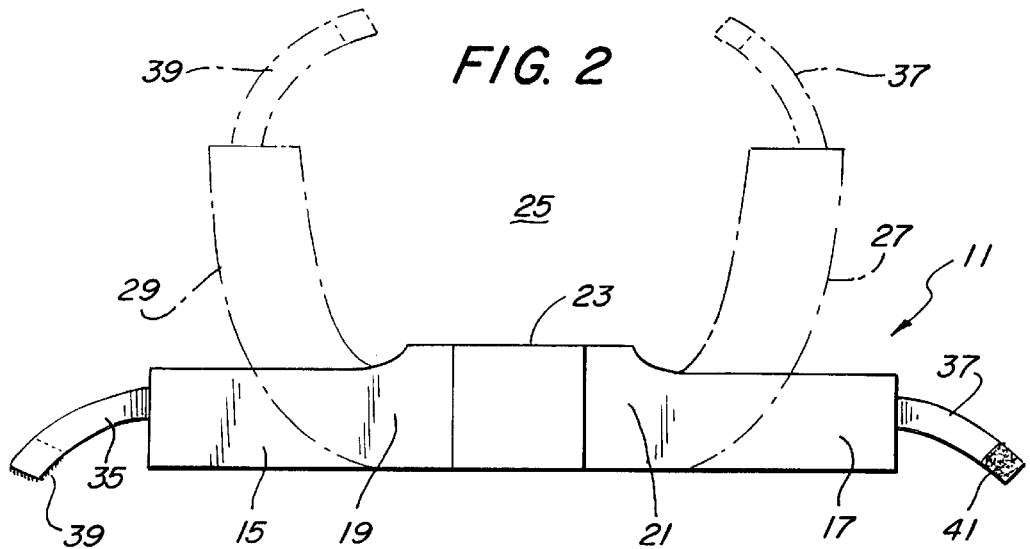
FIG. 2 is a top view of the collar of FIG. 1.
Figure 4:
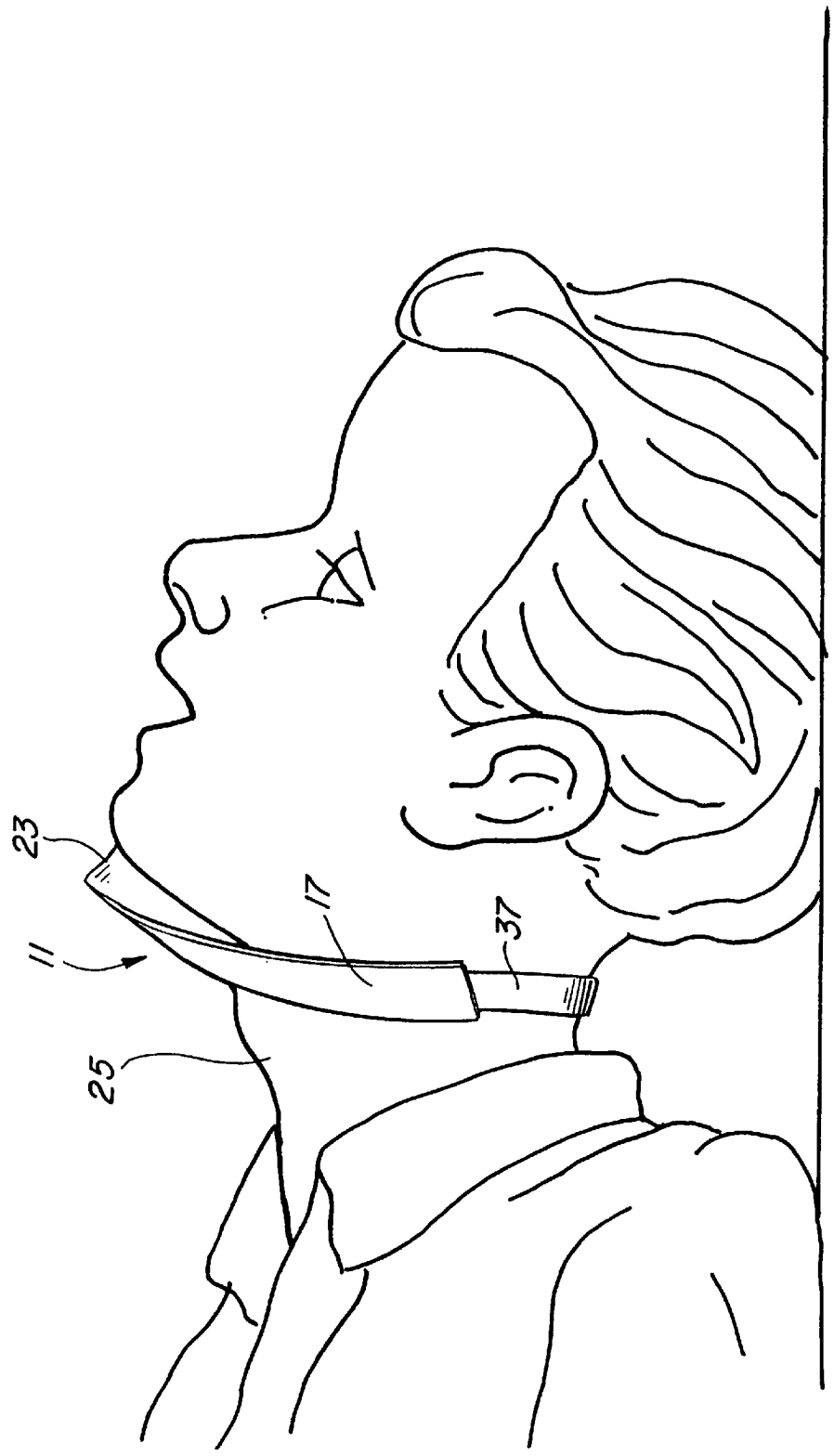
FIG. 4 is a side view of a patient illustrating application of a cervical collar embodiment.

A cervical collar 11 according to a preferred embodiment of the invention is illustrated in FIGS. 1, 2 and 4. As seen in FIGS. 1 and 2, the collar 11 includes a flat bottom surface 13 and first and second arms 15, 17. The arms 15, 17 are preferably equal in length and of identical rectangular cross-section. The arms 15, 17 further meet with respective curved upper surfaces 19, 21, each of which curves upwardly to meet a flat chin support surface 23. The chin support surface 23 is preferably planar and parallel to the planar bottom surface 13. The chin support surface 23 may also be slightly convex or otherwise contoured to more conformably mate with a chin, if desired.

Figure 3:
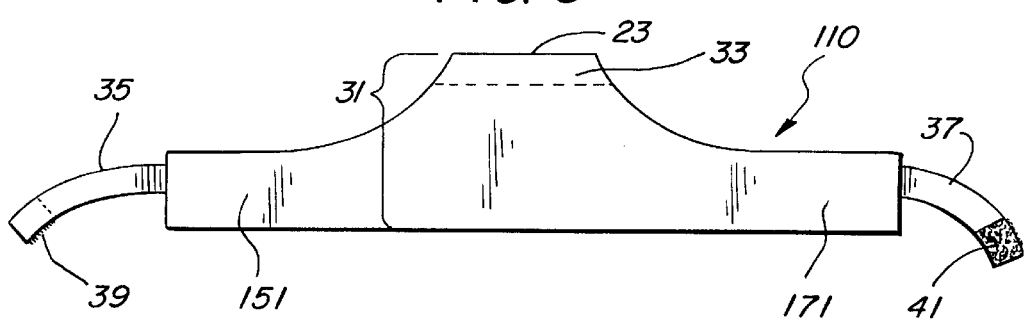
FIG. 3 is a front view illustrating an alternative embodiment.

The entire collar 17 is preferably fabricated as a single foam piece, which exhibits sufficient flexibility to permit the arms 15, 17 to be wrapped around a patient's neck 25, as illustrated in FIG. 4 and by phantom lines 27, 29 in FIG. 2. Such material may exhibit a sponge-like consistency and resiliency. FIG. 3 illustrates an alternate embodiment, wherein the chin support portion 31 of a collar 110 includes a foam portion 33, which is stiffer than the foam comprising the arms 151, 171. The collar 110 may otherwise be constructed in the same manner as the collar 11 of FIGS. 1 and 2.

In order to retain the collar 11 in place, suitable straps 35, 37 may be provided with hook and loop (Velcro#) fastening components 39, 41 at each end for ease of attachment and removal about the neck of the patient.

In known procedures, to help victims in respiratory arrest for any reason, the rescuer manually performs the "chin lift" maneuver to open and maintain a patient's airway. As noted above, this procedure has been also conventionally utilized in the post-anesthesia period on an anesthetized patient to open and maintain the patient's airway. According to the preferred embodiment, the cervical collar 11 is placed about the neck and lifts the angle of the lower jaw upward by placing moderate pressure under the tip of the chin, thereby tilting the head backward and hyperextending the neck. This maneuver aligns the oral pharyngeal and tracheal axis and opens the patient's airway for effective ventilation. It will be noted that the distance (width) between the chin support surface 23 and the bottom surface 13 of the collar is selected to insure the proper tilt of the lower jaw to achieve airway opening. If desired, a set of different sizes of collars to accommodate differing sized patients can be provided. The cervical collar, according to the preferred embodiments, allows for a very safe, effective and easy way to maintain an open airway without interruption, a result that is extremely beneficial when resuscitating a patient.

Those skilled in the art will appreciate that various adaptations and modifications of the just-described preferred embodiments can be configured without departing from the scope and spirit of the invention. Therefore, it is to be understood that within the scope of the appended claims, the invention may be practiced other than as specifically described herein.

What is claimed is:

1. An airway opening device, comprising:
    a collar having first and second portions formed of flexible material and shaped to wrap about the neck of a patient; and
    a central portion located between the first and second portions and shaped to be positioned on the patient parallel to the patient's neck so as to apply sufficient pressure to the tip of the patient's chin to tilt the patient's head backward, thereby opening the patient's airway, said central portion comprising a first foam region and a second foam region, the first foam region being stiffer than the second.

2. The device of claim 1 wherein said first and second portions comprise first and second arms of a width narrower than a width of said central portion.

3. The device of claim 2 further including first and second straps attached respectively to said first and second arms and connectable together to retain said collar in position about the neck of the patient.

4. The device of claim 1 wherein said collar and central portion are further so shaped as to permit turning of the reclining patient's head while said device is holding said airway open.

5. An airway opening device, comprising:
   a collar having first and second portions formed of flexible material and shaped to wrap about the neck of a patient; and
   a central portion located between the first and second portions and shaped to be positioned on a reclining patient parallel to the patient's neck, said central portion being defined at a lower end by a bottom surface and at an upper end by a chin support surface, the distance between the chin support surface and the bottom surface being selected to tilt the lower jaw of the reclining patient so as to achieve opening of said airway,
   wherein said central portion comprises a first foam region and a second foam region, the first foam region being stiffer than the second.

6. The device of claim 5 wherein said first and second portions comprise first and second arms of a width narrower than a width of said central portion.

7. The device of claim 6 further including first and second straps attached respectively to said first and second arms and connectable together to retain said collar in position about the neck of the patient.

8. The device of claim 5 wherein said collar and central portion are further so shaped as to permit turning of the reclining patient's head while said device is holding said airway open.

9. An airway opening device, comprising:
   a collar having first and second portions formed of flexible material and shaped to wrap about the neck of a patient; and
   a central portion means located between the first and second portions, said central portion means having a bottom surface and a chin support surface, said central portion means being shaped to be positioned with said bottom surface abutting a portion of a reclining patient's neck so as to apply force parallel to said patient's neck, toward and on the tip of said patient's chin so as to tilt said patient's head backward, thereby opening said patient's airway,
   wherein said central portion comprises a first foam region and a second foam region, the first foam region being stiffer than the second.

10. The device of claim 9 wherein said first and second portions comprise first and second arms of a width narrower than a width of said central portion.

11. The device of claim 10 further including first and second straps attached respectively to said first and second arms connectable together to retain said collar in position about the neck of the patient.

12. The device of claim 9 wherein said collar and central portion are further so shaped as to permit turning of the reclining patient's head while said device is holding said airway open.

* * * * *